(12) United States Patent
Elahi (10) Patent No.: US 9,555,180 B2
(45) Date of Patent: Jan. 31, 2017

(54) SYSTEMS AND METHODS FOR REMOVING AIR FROM THE PATIENT'S PERITONEAL CAVITY

(75) Inventor: Bijan Elahi, Lake Forest, IL (US)

(73) Assignees: Baxter International Inc., Deerfield, IL (US); Baxter Healthcare SA, Glattpark (Opfikon) (CH)

(*) Notice: Subject to any disclaimer, the term of this patent is extended or adjusted under 35 U.S.C. 154(b) by 504 days.

(21) Appl. No.: 12/275,965

(22) Filed: Nov. 21, 2008

(65) Prior Publication Data

US 2010/0130919 A1   May 27, 2010

(51) Int. Cl.
| | |
|---|---|
| A61M 1/00 | (2006.01) |
| A61M 1/28 | (2006.01) |
| A61M 39/18 | (2006.01) |
| A61M 39/22 | (2006.01) |
| A61M 39/24 | (2006.01) |
| A61M 39/00 | (2006.01) |

(52) U.S. Cl.
CPC ............ *A61M 1/28* (2013.01); *A61M 1/288* (2014.02); *A61M 39/18* (2013.01); *A61M 39/22* (2013.01); *A61M 39/24* (2013.01); *A61M 2039/0009* (2013.01)

(58) Field of Classification Search
CPC ........ A61M 1/28; A61M 1/288; A61M 39/18; A61M 39/24; A61M 39/22; A61M 2039/0009; A61M 39/10; A61M 39/20; A61M 2039/0241; A61M 2039/0255; A61M 2039/0276; A61M 2039/085; A61M 2039/205; A61J 15/0015; A61J 15/0026

USPC ......... 604/29, 502, 284, 126, 6.09, 533–537
See application file for complete search history.

(56) References Cited

U.S. PATENT DOCUMENTS

| | | |
|---|---|---|
| 1,578,517 A | 3/1926 | Hein |
| 2,210,098 A | 8/1940 | Ravenscroft |
| 2,999,499 A | 9/1961 | Willet |
| 3,134,380 A | 5/1964 | Armao |
| 3,135,261 A | 6/1964 | Carroll |
| 3,447,161 A | 6/1969 | Weikel |
| 3,502,097 A | 3/1970 | Muller |
| 3,630,199 A | 12/1971 | Gangarosa et al. |

(Continued)

FOREIGN PATENT DOCUMENTS

| | | |
|---|---|---|
| CA | 1105959 | 7/1981 |
| CA | 1256343 | 6/1989 |

(Continued)

OTHER PUBLICATIONS

International Preliminary Report on Patentablility for PCT/US2009/065375 dated Sep. 29, 2010.

(Continued)

*Primary Examiner* — Bhisma Mehta
*Assistant Examiner* — Laura Schell
(74) *Attorney, Agent, or Firm* — K&L Gates LLP (57) ABSTRACT

A peritoneal dialysis ("PD") connection apparatus includes a first connector for connecting to a PD fluid fill line; a second connector in fluid communication with the first connector, the second connector including a filter configured to allow air but not fluid to pass through the filter; and an air-tight cap manually removeable and resealable to the second connector so as to selectively expose the filter to allow air trapped in a patient's peritoneum to be vented to atmosphere.

16 Claims, 8 Drawing Sheets

(56) References Cited

U.S. PATENT DOCUMENTS

| | | | |
|---|---|---|---|
| 3,659,602 A | 5/1972 | Cloyd |
| 3,797,486 A | 3/1974 | Shaps |
| 3,858,580 A | 1/1975 | Ogle |
| 3,861,388 A | 1/1975 | Vaughn |
| 3,974,832 A | 8/1976 | Kruck |
| 3,976,073 A | 8/1976 | Quick et al. |
| 3,986,508 A | 10/1976 | Barrington |
| 3,994,293 A | 11/1976 | Ferro |
| 4,005,710 A | 2/1977 | Zeddies et al. |
| 4,019,512 A | 4/1977 | Tenczar |
| 4,040,420 A | 8/1977 | Speer |
| 4,079,738 A | 3/1978 | Dunn et al. |
| 4,128,098 A | 12/1978 | Bloom et al. |
| 4,149,535 A | 4/1979 | Volder |
| 4,161,949 A | 7/1979 | Thanawalla |
| 4,187,846 A | 2/1980 | Lolachi et al. |
| 4,191,183 A | 3/1980 | Mendelson |
| 4,201,208 A | 5/1980 | Cambio, Jr. |
| 4,214,779 A | 7/1980 | Losell |
| 4,219,912 A | 9/1980 | Adams |
| 4,256,106 A | 3/1981 | Schoor |
| 4,257,416 A | 3/1981 | Prager |
| 4,294,249 A | 10/1981 | Sheehan et al. |
| 4,296,949 A | 10/1981 | Muetterties et al. |
| 4,306,705 A | 12/1981 | Svensson |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard |
| 4,362,156 A | 12/1982 | Feller, Jr. et al. |
| 4,392,851 A | 7/1983 | Elias |
| 4,405,312 A | 9/1983 | Gross et al. |
| 4,425,113 A | 1/1984 | Bilstad |
| 4,432,764 A | 2/1984 | Lopez |
| 4,432,765 A | 2/1984 | Oscarsson |
| 4,432,766 A * | 2/1984 | Bellotti et al. ................ 604/535 |
| 4,439,193 A | 3/1984 | Larkin |
| 4,457,749 A | 7/1984 | Bellotti et al. |
| 4,508,367 A | 4/1985 | Oreopoulos et al. |
| 4,511,359 A | 4/1985 | Vaillancourt |
| 4,512,766 A | 4/1985 | Vailancourt |
| 4,526,572 A | 7/1985 | Donnan et al. |
| 4,551,146 A | 11/1985 | Rogers |
| 4,564,054 A | 1/1986 | Gustavsson |
| 4,607,868 A | 8/1986 | Harvey et al. |
| 4,610,469 A | 9/1986 | Wolff-Mooij |
| 4,617,012 A | 10/1986 | Vaillancourt |
| 4,620,845 A | 11/1986 | Popovich et al. |
| 4,623,327 A | 11/1986 | Mahurkar |
| 4,624,664 A | 11/1986 | Peluso et al. |
| 4,645,494 A | 2/1987 | Lee et al. |
| 4,655,762 A | 4/1987 | Rogers |
| 4,668,217 A | 5/1987 | Isono |
| 4,673,400 A | 6/1987 | Martin |
| 4,675,004 A | 6/1987 | Hadford et al. |
| 4,701,159 A | 10/1987 | Brown et al. |
| 4,725,267 A | 2/1988 | Vaillancourt |
| 4,738,668 A * | 4/1988 | Bellotti et al. ................ 604/533 |
| 4,743,243 A * | 5/1988 | Vaillancourt ................ 604/405 |
| 4,752,292 A | 6/1988 | Lopez et al. |
| 4,770,652 A | 9/1988 | Mahurkar |
| 4,793,637 A | 12/1988 | Laipply et al. |
| 4,810,241 A | 3/1989 | Rogers |
| 4,816,221 A | 3/1989 | Harvey et al. |
| 4,820,288 A | 4/1989 | Isono |
| 4,842,582 A | 6/1989 | Mahurkar |
| 4,895,570 A | 1/1990 | Larkin |
| 4,917,668 A | 4/1990 | Haindl |
| 4,932,944 A | 6/1990 | Jagger et al. |
| 4,941,517 A | 7/1990 | Galloway |
| 4,946,445 A | 8/1990 | Lynn |
| 4,964,855 A | 10/1990 | Todd et al. |
| 4,981,469 A | 1/1991 | Whitehouse et al. |
| 4,998,713 A | 3/1991 | Vaillancourt |
| 4,998,921 A | 3/1991 | Vickroy et al. |
| 5,009,636 A | 4/1991 | Wortley et al. |
| 5,069,225 A | 12/1991 | Okamura |
| 5,100,394 A | 3/1992 | Dudar et al. |
| 5,122,123 A | 6/1992 | Vaillancourt |
| 5,137,524 A | 8/1992 | Lynn et al. |
| 5,153,489 A | 10/1992 | Unsworth et al. |
| 5,158,554 A | 10/1992 | Jepson et al. |
| 5,167,648 A | 12/1992 | Jepson et al. |
| 5,171,234 A | 12/1992 | Jepson et al. |
| 5,188,593 A | 2/1993 | Martin |
| 5,190,534 A | 3/1993 | Kendell |
| 5,195,992 A | 3/1993 | Dudar et al. |
| 5,199,947 A | 4/1993 | Lopez et al. |
| 5,200,575 A | 4/1993 | Sheehan |
| 5,211,638 A | 5/1993 | Dudar et al. |
| 5,242,425 A | 9/1993 | White et al. |
| 5,263,930 A | 11/1993 | Ensminger |
| 5,269,764 A | 12/1993 | Vetter et al. |
| 5,279,605 A | 1/1994 | Karrasch et al. |
| 5,290,254 A | 3/1994 | Vaillancourt |
| 5,344,414 A | 9/1994 | Lopez et al. |
| 5,377,694 A | 1/1995 | Bark |
| 5,378,230 A | 1/1995 | Mahurkar |
| 5,401,066 A | 3/1995 | Remsburg |
| 5,437,650 A | 8/1995 | Larkin et al. |
| 5,456,675 A | 10/1995 | Wolbring et al. |
| 5,489,278 A | 2/1996 | Abrahamson |
| 5,501,676 A | 3/1996 | Niedospial et al. |
| 5,507,733 A | 4/1996 | Larkin et al. |
| 5,518,276 A | 5/1996 | Gunderson |
| 5,549,583 A | 8/1996 | Sanford et al. |
| 5,571,093 A | 11/1996 | Cruz et al. |
| 5,607,392 A | 3/1997 | Kanner |
| 5,620,427 A | 4/1997 | Werschmidt et al. |
| 5,688,254 A | 11/1997 | Lopez et al. |
| 5,743,892 A | 4/1998 | Loh et al. |
| 5,776,116 A | 7/1998 | Lopez et al. |
| 5,782,808 A | 7/1998 | Folden |
| 5,810,398 A | 9/1998 | Matkovich |
| 5,855,398 A | 1/1999 | Reinholz |
| 5,954,708 A | 9/1999 | Lopez et al. |
| 5,971,958 A | 10/1999 | Zhang |
| 6,027,489 A | 2/2000 | Galato |
| 6,086,575 A | 7/2000 | Mejslov |
| 6,183,465 B1 | 2/2001 | Meier et al. |
| 6,193,283 B1 | 2/2001 | Pickett, Jr. et al. |
| 6,193,697 B1 | 2/2001 | Jepson et al. |
| 6,234,544 B1 | 5/2001 | Bartholomew |
| 6,293,291 B1 | 9/2001 | Sperlich et al. |
| 6,406,470 B1 | 6/2002 | Kierce |
| 6,508,810 B1 | 1/2003 | Ouchi et al. |
| 6,589,251 B2 | 7/2003 | Yee et al. |
| 6,612,622 B2 | 9/2003 | Andre et al. |
| 6,652,509 B1 | 11/2003 | Helgren et al. |
| 6,673,059 B2 | 1/2004 | Guala |
| 2002/0023504 A1 | 2/2002 | Austin |
| 2002/0082586 A1 | 6/2002 | Finley et al. |
| 2002/0095210 A1 | 7/2002 | Finnegan et al. |
| 2002/0123715 A1 | 9/2002 | Sorenson et al. |
| 2003/0144647 A1 | 7/2003 | Miyahara |
| 2003/0176852 A1 | 9/2003 | Lynch et al. |
| 2004/0034334 A1 | 2/2004 | Ruddell et al. |

FOREIGN PATENT DOCUMENTS

| | | |
|---|---|---|
| DE | 84 25 197 | 10/1985 |
| EP | 0 092 528 | 10/1983 |
| EP | 0 113 677 | 8/1984 |
| EP | 0 268 480 | 5/1988 |
| EP | 0 554 722 | 8/1993 |
| EP | 1 772 161 | 4/2007 |
| GB | 2 063 684 | 6/1981 |
| GB | 2 067 075 | 7/1981 |
| JP | 09192216 A | 7/1997 |
| JP | 10248924 A | 9/1998 |
| JP | 11057419 A | 3/1999 |
| JP | 11-128359 | 5/1999 |
| JP | 2000014772 A | 1/2000 |
| JP | 2000140099 A | 5/2000 |

(56) References Cited

FOREIGN PATENT DOCUMENTS

| WO | WO 83/00447 | 2/1983 |
| WO | WO 83/00812 | 3/1983 |
| WO | WO 95/15194 | 6/1995 |
| WO | WO 97/00095 | 1/1997 |
| WO | WO 97/35634 | 10/1997 |

OTHER PUBLICATIONS

Japanese Office Action issued Oct. 30, 2013 in corresponding Japanese Patent Application No. 2011-537662.

* cited by examiner

Empty
Pigtail
Tube

FIG. 6B

One-way
Valve and
Spike are
Assembled

FIG. 6C

Fluid is
Injected
in the
Pigtail

FIG. 6D

Membrane/
Sleeve is
Inserted at
Pigtail Top

FIG. 9

SYSTEMS AND METHODS FOR REMOVING AIR FROM THE PATIENT'S PERITONEAL CAVITY

BACKGROUND

The present disclosure relates to medical fluid treatment and in particular to the prevention and removal of air from a patient's peritoneal cavity.

One problem that patients undergoing peritoneal dialysis ("PD") treatment or a laparoscopic procedure can encounter is air becoming trapped in the patient's peritoneal cavity or pneumoperitoneum. Introduction of air into the patient's peritoneal cavity can cause pain. The gas can exert pressure on the patient's diaphragm and affect breathing. The air or gas pressure can also exert pressure on the patient's phreuic nerve, which produces a sensation of pain that may extend all the way to the patient's shoulders.

One source of air entering the patient is air from solution bag lines. The air becomes trapped in the solution bag lines (sometimes called pigtails), for example, during manufacture, shipping or upon connection of the lines for treatment. If the solution bag lines are not purged properly, the trapped air can enter the patient. This is especially true for longer pigtail or solution bag lines. A first need accordingly exists to prevent air from becoming trapped in the patient line during manufacture or therapy setup.

When the patient does experience air trapped in his/her peritoneal cavity, current practice is to wait for the gas to be absorbed by the patient's body. Such procedure can take a number of days depending on the amount of air that needs to be absorbed. Another need therefore exists for quickly removing air from the patient's peritoneal cavity when such situation does occur, so that the patient does not have to wait for his/her body to absorb the air volume.

SUMMARY

The present disclosure provides multiple embodiments for preventing air from entering tubes or pigtails that extend from peritoneal dialysis ("PD") solution bags. Multiple embodiments are also provided for removing air from the solution bag tube prior to therapy hookup. Also described herein is an apparatus and method for removing air from the patient's peritoneal cavity when such an entrapment unfortunately occurs.

In a first embodiment, an autoconnection device is provided having a first position in which a U-shaped or semicircular shunt spike spikes or pierces the supply and the drain bags simultaneously to allow a portion of fresh solution to flow from the supply bag to the drain bag to prime both supply and drain bag lines and purge air from same. The lines are each fed through an occluder valve, such as an electromechanical pinch valve. Once the lines are pierced, the valves are each opened to allow the supply bag and line to communicate with the drain bag and line to prime the supply line.

Next, the occluder valves are closed and the autoconnection device rotates or otherwise moves the shunt spike away from the closed-off supply and drain lines. The autoconnection device then connects the patient's transfer set to the supply line. Such disconnection and connection can be made under ultraviolet radiation to ensure the sterility of the final supply connection to the patient. Therapy can now proceed.

In a second embodiment, a fluid receptacle or reservoir is placed on the supply line or pigtail, so as to be in communication with the fluid located in the supply line. The receptacle is made of the same material as the supply line tubing in one embodiment and is relatively flexible, strong and resilient. The receptacle is located at or near the connector or distal end of the supply line, opposite the bag or container end of the supply line. The receptacle or reservoir is an at least substantially circular pillow in one embodiment.

The reservoir fills with fluid, such that the patient can press the reservoir to push the fluid and thus the air trapped in the fluid towards the supply bag. When the patient releases the reservoir, the reservoir expands and fills again with fresh dialysis fluid, so that the reservoir can be pressed again to further move the trapped air into the supply container. This procedure is repeated until the patient visually determines that all the air has been pushed to the supply bag and collected at an air collection portion of the bag. The supply line can be pre-connected to at least one of a supply bag and a disposable pumping cassette.

In a third embodiment, the autoconnection device holds the connector end of the supply line and a disposable air trap. The autoconnect device connects (i) the patient transfer set to one side of the air trap and (ii) the fluid line to the other side of the air trap. The air trap has a fluid inlet, which is located near the bottom of the reservoir in one configuration. When supply fluid reaches the reservoir, air entrained in the fluid accumulates within the air trap, allowing air to migrate vertically upwardly in the air trap and to degas into the vertically elevated air collection area of the trap or reservoir.

In one embodiment, the patient's transfer set spikes the air trap, while the air trap spikes the fill bag line simultaneously or virtually simultaneously. Here, the air trap is a separate disposable piece that is inserted into the autoconnection device. The autoconnection device also serves to support the disposable for spiking. Making the air trap separate from the fill bag allows the autoconnection device to hold the air trap in an operating position and the fill bag line to be moved freely to the air trap.

In a fourth embodiment, the supply bag includes a separate fill tube and a one-way valve is placed in the supply bag line. During manufacturing, the fill bag is filled from the fill tube. Eventually, supply fluid flows from the supply bag to the supply bag line through the one-way valve, priming the line and purging air from it. The one-way valve prevents any liquid that contacts non-sterile air while the supply bag line is open for purging from flowing back into the supply bag. The valve also prevents air in the bag from entering the supply line because fluid from the supply line cannot flow to the bag to displace such air. When the supply bag line is fully primed and purged of air, the line is capped, making the supply bag ready for use. The entire assembly can be sterilized using gamma radiation or steam, for example.

In a fifth embodiment, which is similar to the fourth embodiment, the supply tube is filled with fluid and primed before being connected to the supply bag. The supply line includes a one-way valve on its proximal or bag end. The line is filled from this end. The one-way valve prevents fluid from exiting the fill end before the supply line is spiked to the bag but allows fresh dialysis to flow from the supply tube through the supply line during use. Because the tube is filled with fluid, there is no room for air to enter the tube. The valve prevents fluid residing within the tube from migrating back into the bag, making room in the tube for air to potentially enter it. The distal or patient end of the supply line is capped when the supply line is fully primed. The proximal end of the supply line is then spiked to the bag. In one embodiment, the entire bag and fill line is sterilized after the supply line is spiked to the bag.

In a sixth embodiment, the supply line is filled with carbon dioxide ("$CO_2$") gas to purge air from the supply bag line prior to its connection to the supply bag. $CO_2$ is heavier than air and is therefore suitable for the inerting or purging of air from the supply tube. $CO_2$ gas is also common to the human body. The patient readily absorbs $CO_2$ gas and exhales same through the patient's lungs. Both the distal (patient) and proximal (bag spike) ends of the supply tube are capped. The spike cap is removed and the supply bag is spiked. The supply bag and supply lines are sterilized after connection.

In a seventh embodiment, a y-connector is provided at the distal or patient end of the supply line. One branch of the y-connector is fitted with a hydrophobic membrane. A one-way or check valve is provided at the proximal end of the supply line. After manufacturing the supply bag and filling bag with fresh dialysate, air may become trapped in the supply line. The hydrophobic membrane fitted at the end of the y-connector allows air but not fluid to escape the supply line. The hydrophobic valve can be capped and uncapped as needed.

The supply bag is suspended vertically with the supply line extending downwardly from the supply bag. Fresh dialysate in the supply bag presses downwardly on the fluid in the supply line, forcing gas pockets through and out of the supply line via the hydrophobic membrane on the bag of the y-connector. The one-way valve prevents air from migrating upwardly into the supply line and supply bag. The hydrophobic fitting of the y-connector is capped when the air purge is completed.

In an eighth embodiment, the patient's transfer set is fitted with a connector having a hydrophobic filter, which again allows air but not liquid to be purged from the patient. A cap is provided that covers the hydrophobic membrane. When the patient feels air in his/her peritoneum, the patient reclines, allowing the air to accumulate towards the exit point of the catheter. The patient removes the air-tight cap, allowing the air inside the peritoneum to escape via the hydrophobic membrane. The patient then replaces the air-tight cap after feeling the discomfort subside. In one embodiment, the patient's catheter includes perforations or holes near the exit point of the catheter (inside the patient, near the stomach wall). The holes or perforations allow air trapped in the peritoneum to flow into the catheter via the holes and travel through the fluid and the hydrophobic membrane to atmosphere.

In light of the above-described embodiments, it is accordingly an advantage of the present disclosure to provide various embodiments for removing air from a supply bag, or preventing air from entering the line, at the time of the manufacturing of the supply bag and the patient line.

It is another advantage of the present disclosure to provide various embodiments for removing air from a supply bag line, or preventing air from entering the line, at the time of connection of the supply line to the patient's transfer set.

It is a further advantage of the present disclosure to provide various embodiments for removing air from a supply bag line that operates with a patient autoconnection device ("PAC").

It is yet another advantage of the present disclosure to provide an apparatus and method for removing air trapped in a patient's peritoneal cavity.

Additional features and advantages are described herein, and will be apparent from the following Detailed Description and the figures.

DETAILED DESCRIPTION

Figure 1A:
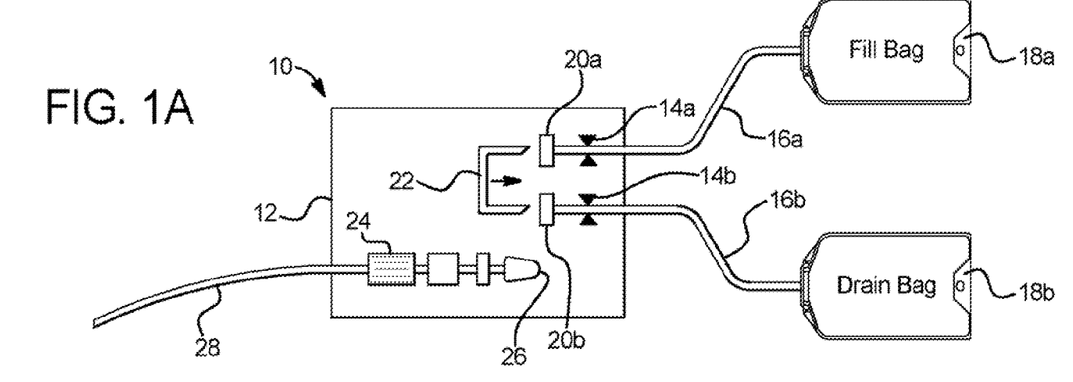
FIGS. 1A and 1B are schematic elevation views illustrating one embodiment of a patient auto connection ("PAC") system having a shunt connector that allows air from a fill container to be delivered drain, the PAC system also connecting the patient's transfer set to the supply line, FIGS. 1A and 1B showing the PAC system in two different states.
Figure 1B:
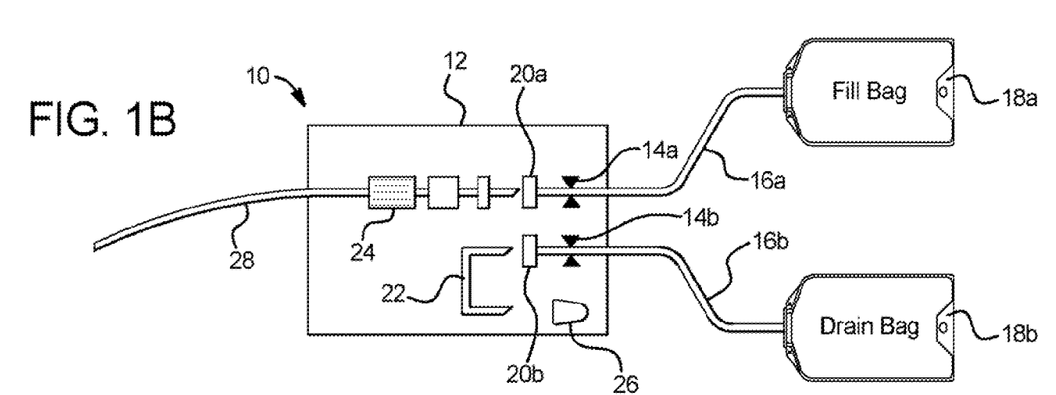

Referring now to the drawings and in particular to FIGS. 1A and 1B, patient auto connection ("PAC") system 10 illustrates one embodiment for removing air from the patient's supply or fill line prior to the patient connecting to such line. PAC system 10 includes a housing 12 that is motorized to automatically rotate or flip components after the supply line has been purged and sterilized to a position such that the patient's transfer set can be automatically connected to the fill or supply line. Housing 12 is configured alternatively to allow the patient to mechanically rotate or flip components after the supply line has been purged and sterilized into a position, such that the patient's transfer set can be connected to the fill or supply line. Various embodiments for automatic and mechanically rotatable PAC systems, which can be modified for use with system 10 are disclosed in U.S. patent application Ser. No. 11/773,750 ("the '750 Application"), entitled "Dialysis System Having Supply Container Autoconnection", filed Jul. 5, 2007, especially at FIGS. 12, 13A to 13I and 14 and associated text (automated); and U.S. patent application Ser. No. 11/773, 795, entitled "Dialysis System Having Dual Patient Line Connection And Prime", filed Jul. 5, 2007, especially at FIGS. 15A to 15E and associated text (manual). Each of the referenced applications is assigned to the assignee of the present disclosure and is incorporated herein expressly by reference.

Priming with system 10 can be performed while undergoing a sterilization process. In one embodiment, sterilization is performed via ultraviolet ("UV") radiation. The '750 Application incorporated above discusses one suitable embodiment for combining the UV irradiator with a PAC device.

Housing 12 includes a fill bag occluder valve 14a and a drain bag occluder valve 14b. Housing 12 can be metal or plastic as desired. Valves 14a and 14b in one embodiment are normally closed, e.g., spring closed, energized open, and are actuated electrically. In an alternative embodiment, valves 14a and 14b are operated pneumatically. Valve 14a is positioned and arranged within housing 12 so as to receive a fill line 16a, which is connected to a fill container 18a. Occluder valve 14b in turn receives a drain bag line 16b, which is connected fluidly to a drain bag 18b.

For any of the embodiments described herein, the fill bag can be made of a suitable medical grade material, such as polyvinal chloride ("PVC"). Tubing 16a and 16b likewise can be made of the same or different medical grade material, such as PVC. Tubes 16a and 16b each terminate at a pierceable cap 20a and 20b, respectively. Caps 20a and 20b are each fitted with a spikeable or pierceable membrane (not illustrated), which holds fluid within tubing 16a or 16b until spiked and allows a sterile connection to be made via a shunt spike 22 upon spiking.

Housing 12 holds shunt spike 22 in a position relative to caps 20a and 20b, such that shunt pike 22 can be translated to simultaneously puncture the pierceable membranes of both caps 20a and 20b. Shunt spike 22 in an embodiment is made of a suitable flexible or rigid medical grade plastic, such as Acrylic or chlorotriflouroethylene ("CTFE"). Shunt spike 22 can have a substantially "U-shape" as shown or alternatively have a "V-shape" and can otherwise be rounded or having straight pieces as desired.

Housing 12 also holds a patient transfer set 24, which is initially capped via a cap 26. Patient transfer set 24 is in turn connected to a patient line 28, which leads to a catheter (not illustrated) inserted into the patient's peritoneal cavity. Patient line 28 can be made of one of the materials described above for fill line 16a and drain line 16b.

In operation, tubes 16a and 16b having unobstructed caps 20a and 20b, respectively, are positioned into housing 12. Occluder valves 14a and 14b are then closed (e.g., deenergized), clamping lines 16a and 16b, respectively. Shunt spike 22 is then mechanically or manually translated, so as to puncture the membranes sealing caps 20a and 20b. The connection of shunt spike 22 to caps 20a and 20b is made such that caps or portions of tubing 16a and 16b are sealed to the ends of shunt spike 22 when connected, and so that liquid cannot escape from the fill line 16a or drain line 16b around shunt spike 22 and into housing 10. Once the sealed connection is made, and occluder valves 14a and 14b are opened, dialysis fluid can flow from supply bag 18a, through supply line 16a, connector 20a, shunt spike 22, connector 20b, and drain line 16b to drain bag 18b. Such action forces any air in supply line 16a to be pushed to drain bag 18b. Once supply line 16a is purged sufficiently, occluder valves 14a and 14b are closed.

The UV radiation in one embodiment takes place just prior to and during the spiking operation of shunt spike 22 to connectors 20a and 20b. Such timing ensures that the spiking of shunt spike 22 to connectors 20a and 20b is done aseptically. The spiking of shunt spike 22 to connectors 20a and 20b is also done electromechanically in one embodiment by snap-fitting shunt spike 22 into a block of housing 12, which is translated via a lead screw, which is turned by an electric motor. To drive shunt spike 22 in a spiking direction, the motor shaft of the motor is turned in a first direction. Once valves 14a and 14b have closed after proper flushing of fill line 16a, the motor drives the motor shaft in the opposite direction, causing the lead screw driven block of housing 12 and shunt spike 22 to be pulled away from connectors 20a and 20b.

At some point during the spiking and flushing operation, cap 26 is removed from transfer set 24. If cap 26 and shunt spike 22 are moved manually, such operation is done with a lid of housing 12 open. The lid of housing 12 is then closed and the UV radiation is applied to irradiate both the exposed end of transfer set 24 and the spike ends of fill tube 16a and drain tube 16b. Otherwise, if cap 26 and shunt spike 22 are removed and moved electromechanically, the electromechanical movement can be done just prior to the movement of either shunt spike 22 or cap 26, here with a lid of housing 12 closed. The automatic removal of cap 26 can again be done via a translated block that is moved on a small lead screw to capture cap 26 and then translated in the opposite direction to pull cap 26 off of transfer set 24. Cap 26 can be held within housing 12 and then reinserted onto transfer set 24 when the patient has filled himself or herself with fresh dialysate from the supply bag 18a.

FIG. 1B illustrates that once cap 26 is removed, shunt spike 22 and transfer set 24 are switched, so that transfer set 24 is now aligned with connector 20a of supply container 18a. The same translation mechanism that drives shunt spike 22 into connector 20a now drives patient transfer set 24 into that connector. The same sealing mechanism of connector 20a that seals about shunt spike 22 also seals about a spike end of transfer set 24. After the sealed connection between transfer set 24 and shunt spike 20a is made, occluder valve 14a is opened, allowing fluid to flow from fill bag 18a through patient transfer set 24 and patient line 28 to the patient's peritoneal cavity. The connection of patient transfer set 24 to connector 20a of the supply line 18a can again be done under UV radiation, so as to kill any pathogens that may be present on the spike end of transfer set 24 prior to insertion into connector 20a.

When the fill to the patient has been completed, occluder valve 14a is closed and the solution is allowed to dwell within the patient for a sufficient amount of time. Afterwards, shunt spike 22 is removed from housing 12 and patient transfer set 24 is rotated or translated into alignment with drain bag connector 20b. Transfer set 24 is then spiked into that connector, allowing the spent or effluent fluid to flow into drain bag 18b once drain valve 14b is opened.

Figure 2:
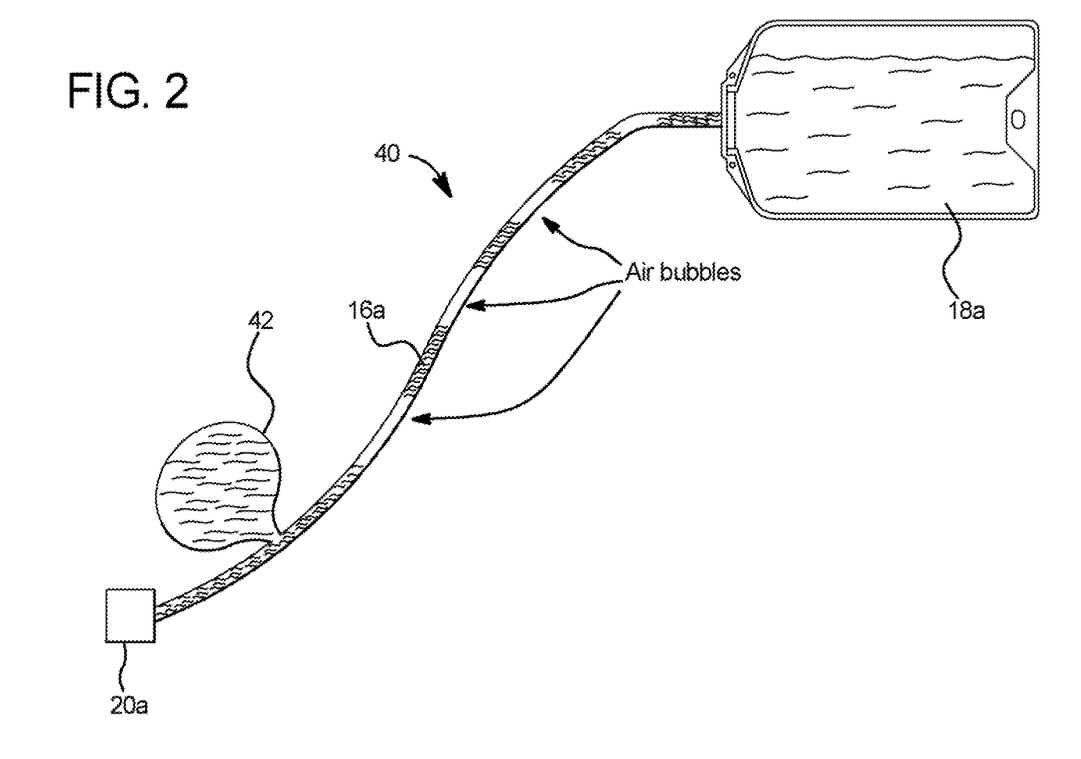
FIG. 2 is a side elevation view showing one embodiment of a fill container and fill container line having a reservoir configured to receive fluid, such that a patient can squeeze the reservoir to drive medical fluid and any air contained therein up the fill container line and into the fill bag before the supply fluid is delivered to the patient.

Referring now to FIG. 2, filling apparatus 40 illustrates another embodiment for removing air from the fill solution, so that the air is not delivered to the patient. Apparatus 40 includes supply line 16a, fill bag 18a and connector 20a, which are at least substantially the same as described above in connection with FIGS. 1A and 1B. The materials for these structures can be any of those discussed above for FIGS. 1A and 1B. Here however, supply line or pigtail 16a includes a flexible reservoir 42, which fills with supply fluid, enabling the patient to squeeze the fluid to build pressure in supply line 16a. Reservoir 42 in one embodiment is attached directly to fill line 16a. For example, reservoir 42 can be welded directly to the fill line. Alternatively, reservoir 42 is formed with fill line 16a. In a further alternative embodiment, reservoir 42 is formed with a connector, which is in turn spliced into fill line 16a or connected to one end of the fill line. For example, reservoir 42 could be formed with connector 20a. The receptacle or reservoir 42 is an at least substantially circular pillow in one embodiment.

Reservoir 42 collects a relatively small amount of fluid. As illustrated, reservoir 42 is located adjacent to or near, if not at the distal end of fill line 16a. After reservoir 42 is filled with fluid, the patient squeezes the reservoir prior to connecting the patient's transfer set to connector 20a. Squeezing reservoir 42 therefore forces fluid and any air trapped therein up patient line 16a and into fill bag 18a. The air is pushed up into fill bag 18a, towards a top or air reservoir portion of the bag. Fill line 16a is connected towards the bottom of the bag 18a, allowing air to migrate to the air reservoir, away from the connection of fill line 16a, such that when connected to fill line 16a, only supply fluid is delivered to the patient. Apparatus 40 can be pre-connected to at least one of a fill bag 18a and a disposable pumping and/or valving cassette (not illustrated).

Figure 3:
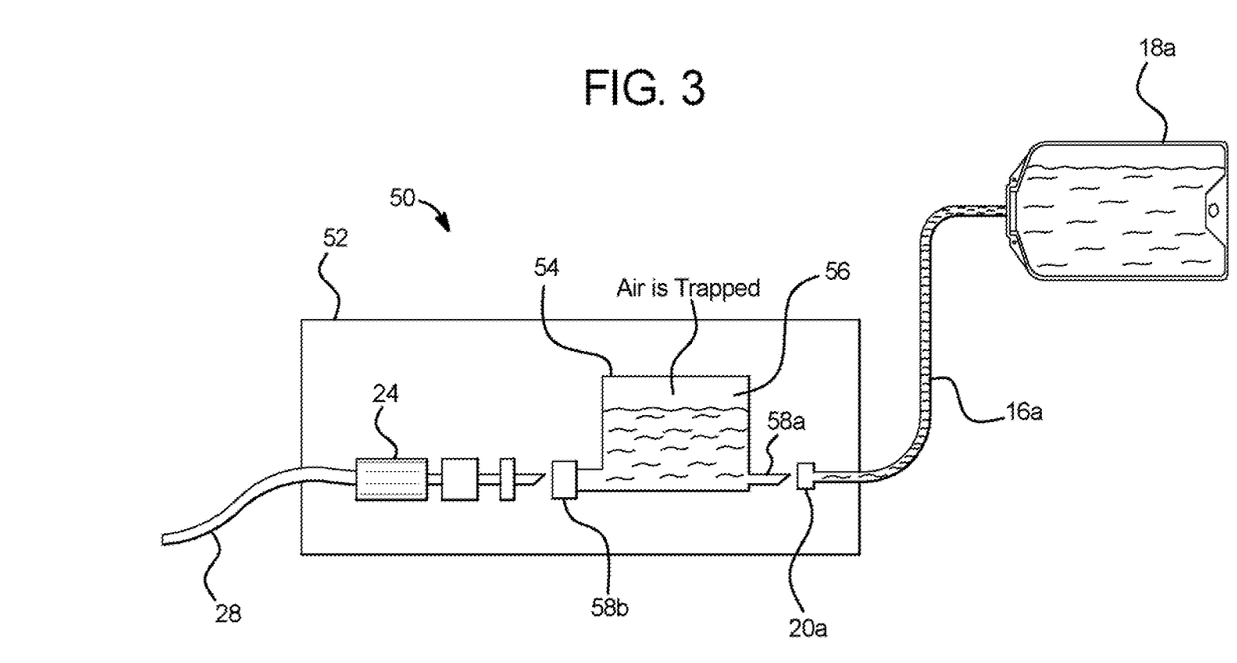
FIG. 3 is a side elevation view of one embodiment of a PAC device having an air trap positioned between a fill bag line and the patient transfer set, such that the air trap can collect air from a pooled supply fluid before the supply fluid is delivered to patient.

Referring now to FIG. 3, PAC system 50 illustrates another embodiment for removing air from the supply line or pigtail 16a prior to delivery of the fresh solution to the patient. PAC system 50 includes a housing 52, which can be metal or plastic, as is the case with housing 12 of system 10. System 50, like system 10, includes a fill bag 18a connected fluidly to a supply line or supply pigtail 16a. Supply line 16a terminates at a sealed and pierceable connector 20a. System 50 also includes a patient transfer set 24, which is connected to a patient line or catheter 28 that runs to the patient's peritoneal cavity. Patient transfer set 24 is initially capped via cap 26, which has been removed for the illustration of FIG. 3.

System 50 further includes an air trap 54, which is held within housing, such that any air coalescing in a reservoir portion 56 of air trap 54 is held elevationally above a spiked fluid inlet 58a and a pierceable connector outlet 58b. Pierceable connector 58b in an embodiment is configured in substantially a same manner as supply line connector 20a. In both cases, the connectors include a pierceable sealing membrane and also apparatus for sealing about either the spike end of patient transfer set 24 or the spike inlet 58a of air trap 54. Although not illustrated, air trap 54 can have one or more internal baffle for aiding in the separation of air from the liquid that pools in the air trap. Suitable configurations for air trap 54 are disclosed in co-pending patent application Ser. No. 11/865,577, entitled "Dialysis Systems Having Air Traps With Internal Structures To Enhance Air Removal"; Ser. No. 11/865,583, entitled "Dialysis Systems Having Air Separation Chambers With Internal Structures To Enhance Air Removal"; Ser. No. 11/865,552, entitled "Dialysis System Having Air Separation Chambers With Internal Structures To Enhance Air Removal"; and 60/976,731, entitled "Fluid And Air Handling In Dialysis Circuit Air Removal System", each filed on Oct. 1, 2007, assigned to the eventual assignee of the present disclosure, the entire contents of each of which are incorporated expressly herein by reference. Air trap 54 can be part of a disposable with a supply line 16a and supply container 18a and/or be connected to a disposable pumping/valving cassette (not illustrated). The Supply line 16a is pre-connected to air trap 54 in one embodiment.

PAC system 50, similar to system 10, can have a UV irradiating source, which irradiates the spike of transfer set 24 and the spike end 58a of air trap 54 and associated connectors 58b and 20a, respectively, just prior to the spiking of connectors 58a and 20a. Housing 52 in one embodiment provides for a single translational movement of patient transfer set 24 to cause a virtual simultaneous spiking of connectors 58b and 20a. If such spiking is done alternatively manually, a cover of housing 52 can be placed over air trap 54 and patient transfer set 24 just after such spiking, at which point the UV radiation source irradiates the spike connections of connectors 58a and 58b. If spiking is performed automatically or electromechanically, the cover of housing 52 is placed over patient transfer set 24 and air trap 54 and UV irradiation is performed just prior to and during the automatic spiking of connectors 58b and 20a. Housing 52 is configured alternatively to carry at least one of a (i) shuttle that moveably connects the patient transfer set to the patient transfer set connector of the air trap and (ii) a shuttle that moveably connects the supply line to the air trap, the at least one shuttle being (a) manually activated and (b) motorized.

After the spiking of the connectors is performed, fresh dialysis fluid flows from fill bag 18a, through fill line 16a, through connector 20 and pools inside air trap 54. Air migrates upwardly in the denser solution and coalesces in upper reservoir 56, such that only fresh solution travels from air trap 54, through patient transfer set 24 and patient line or catheter 28 into the patient's peritoneum.

Figure 4:
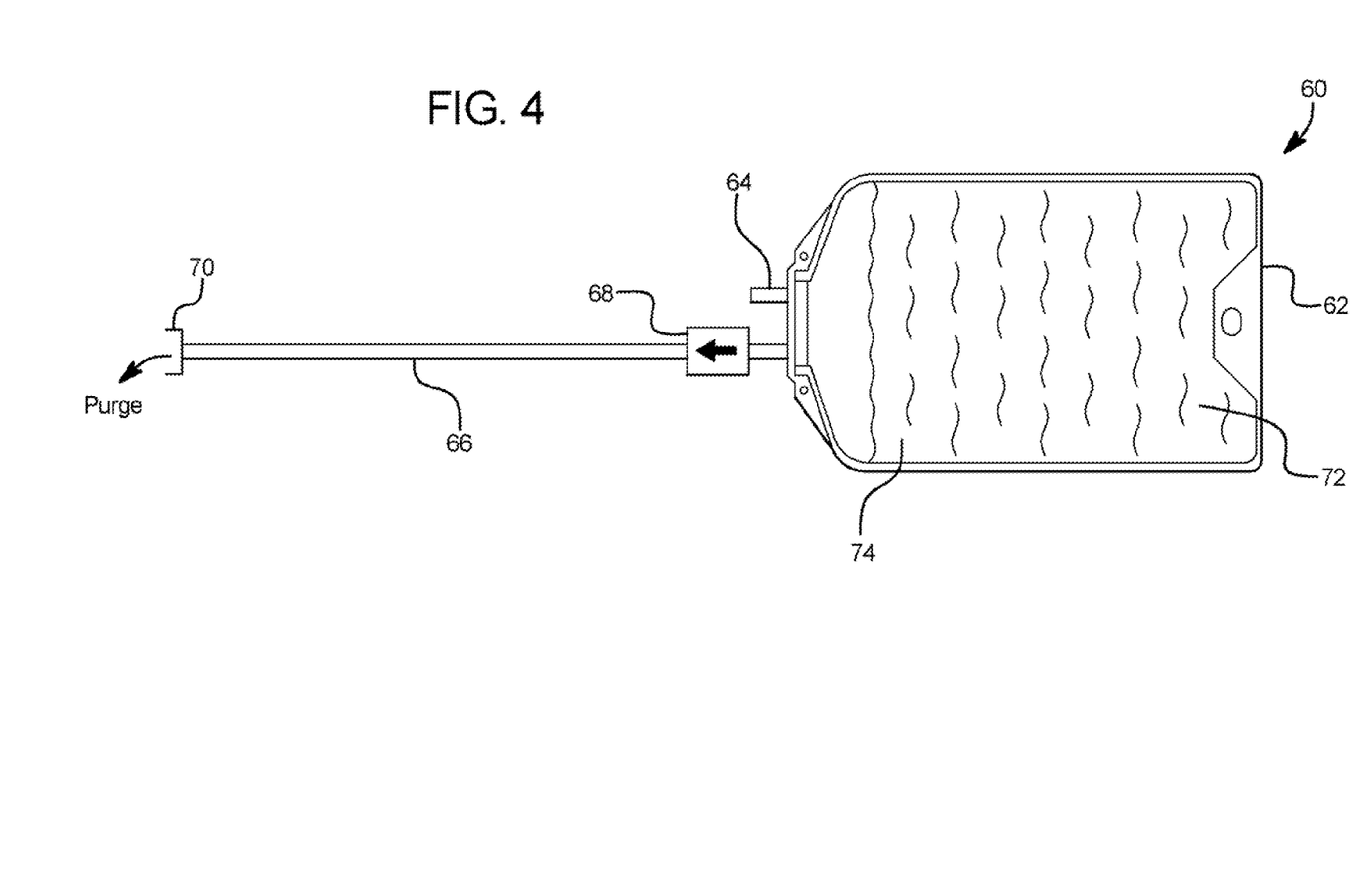
FIG. 4 is a side elevation view of one embodiment of a fill bag having a fill tube inlet and a supply fluid outlet connected via a one-way or check valve to a supply fluid line, the configuration allowing the fill container to act as an air trap, preventing air from being delivered via the supply line to the patient.

Referring now to FIG. 4, apparatus 60 illustrates another embodiment for preventing air from being delivered to the patient's peritoneum during a patient fill. Apparatus 60 includes an alternative fill container or fill bag 62 having a fill port 64. An alternative fill line 66 is provided, which includes an inline check valve or one-way valve 68, which allows fresh dialysis fluid to only flow from fill bag 62 towards a purge connector 70 located at a distal end of fill line 66. Fill bag 62 and fill line 66 are made of any of the materials discussed above for bag 18a and fill line 16a. Fill port 64 in one embodiment is a rigid piece of tubing that is welded to fill bag 62. Check valve 68 can be welded directly to a similar port extending from fill bag 62. Alternatively, check valve 68 is spliced into fill line 66, which is then sealed to fill bag 62. Purge connector 70 in an embodiment is a portion of connector 20a, which after the manufacturing sequence next described is capped with a pierceable membrane to form a connector 20a.

During manufacturing, fill bag 62 is filled with fresh fluid via fill port 64. Fluid fills bag 62 and becomes pressurized, forcing one way valve 68 to open, allowing fluid to flow through fill line 66, pushing air out of the fill line via purge connector 70. In an embodiment, the manufacturing process is performed while fill tube 64, check valve 68 and supply line 66 are housed elevationally above fill bag 62. Such arrangement allows the fill bag at its lower end 72 to be filled first, pushing air towards a top end 74 of fill bag 62. When the entire fill bag 62 and fill line 66 are completely filled with fresh dialysis fluid, fill port 64 is capped, which can be done under a sterilized or sterilizing environment.

One-way valve 68 during prime prevents fluid in line 66 from reentering fill bag 62 once the air has been pushed past one-way valve 68. Thus any air trapped in the fluid held within fill line 66 cannot re-center bag 62. Also, fluid cannot flow from line 66 to bag 62, creating space that can potentially be filled with air. At the end of the patient fill, purge connector 70 is likewise capped with a pierceable membrane to form connector 20a. Such procedure is also performed under a sterilized environment in one embodiment. The entire assembly can then be sterilized via a suitable process, such as gamma radiation, ethylene oxide or steam, at the manufacturing facility.

Figure 5:
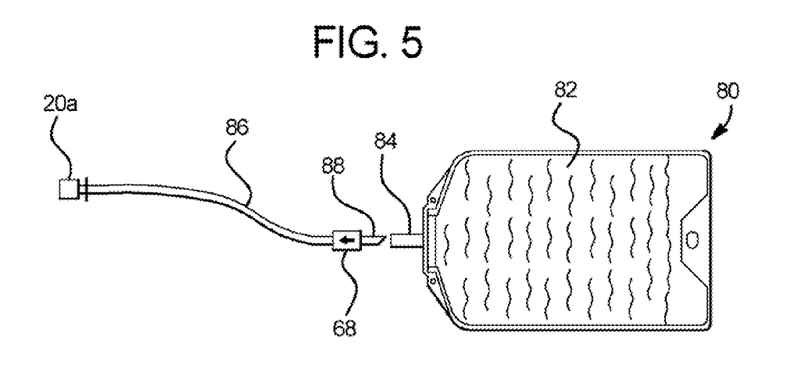
FIG. 5 is an elevation view of one embodiment of a solution bag connected to a supply tube that has been pre-primed and capped so as not to deliver air to the patient.

Referring now to FIG. 5, apparatus 80 illustrates still another alternative embodiment for preventing air from being delivered to the patient's peritoneum during PD fill. Apparatus 80 includes a supply bag or container 82 having a port 84 sealed via a pierceable membrane. Port 84 is spiked with a spike 88 of a fill line 86, which has been filled and purged of air. Once fill line 86 is connected to solution container 82, solution container 82 can be hung such that pierceable port 84 is located elevationally at the bottom of solution bag 82, and such that only fluid and not air is delivered to the patient. As illustrated, fill line 86 is connected to a check or one way-valve 68, which in turn is connected to a spike 88 that spikes a membrane seal of port 84, e.g., under a sterilized environment. A distal end of supply line 86 is capped via a pierceable membrane cap 20*a*.

Figure 6A:
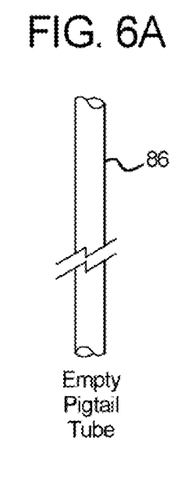
FIGS. 6A to 6D illustrate different steps in priming the patient's supply line used in connection with the embodiment illustrated in FIG. 5.
Figure 6B:
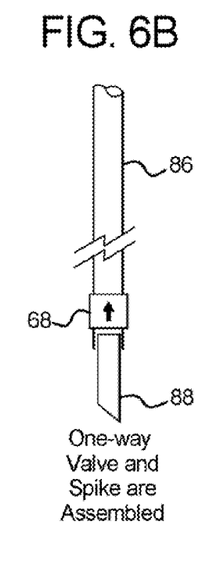
Figure 6C:
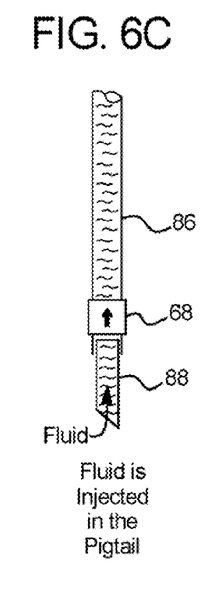
Figure 6D:
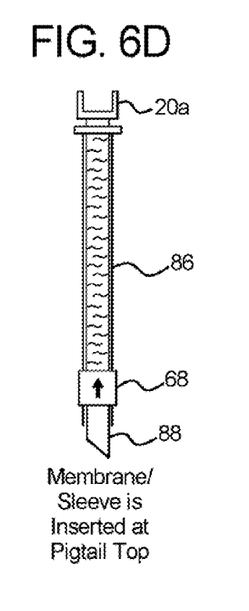

FIGS. 6A to 6D show the filling and flushing of supply line 86. FIG. 6A illustrates an empty section of pigtail tubing 86. FIG. 6B illustrates the sealed connection of one way-valve 68 to tubing 86 and an additional sealed connection of a spike 88 to one way valve 68. In FIG. 6C, fluid is injected into spike 88, which flows through check valve 68 and supply line tubing 86 until the supply line is filled completely. Tube 86 is positioned vertically in the embodiment illustrated in FIG. 6C, such that fluid injected from the bottom pushes air out the top of the tubing 86. The Check valve 68 then prevents the filled fluid from flowing out of fill line 68, through the check valve. FIG. 6D illustrates that after solution tube 86 has been filled completely, cap 20*a* having a pierceable membrane is sealed to a distal end of supply tube 86, e.g., under a sterilized environment. The entire apparatus 80 (connected or not connected) can then be sterilized via gamma radiation or steam sterilization, for example.

FIG. 5 illustrates the final step in which the solution-filled supply tube 86 is spiked into membrane sealed port of 84 of supply container 82. Port 84 is configured to seal about spike 88. Check valve 68 prevents accidental movement of fluid from the tube to the bag, which could facilitate the entry of the air from bag to the tube. The check valve ensures that no room becomes available in the tube for air, e.g., during shipping. It is contemplated to package and ship apparatus 80 with filled tube 86 separated from container 82 or to package and ship apparatus 80 with filled tube 86 connected to container 82.

Figure 7:
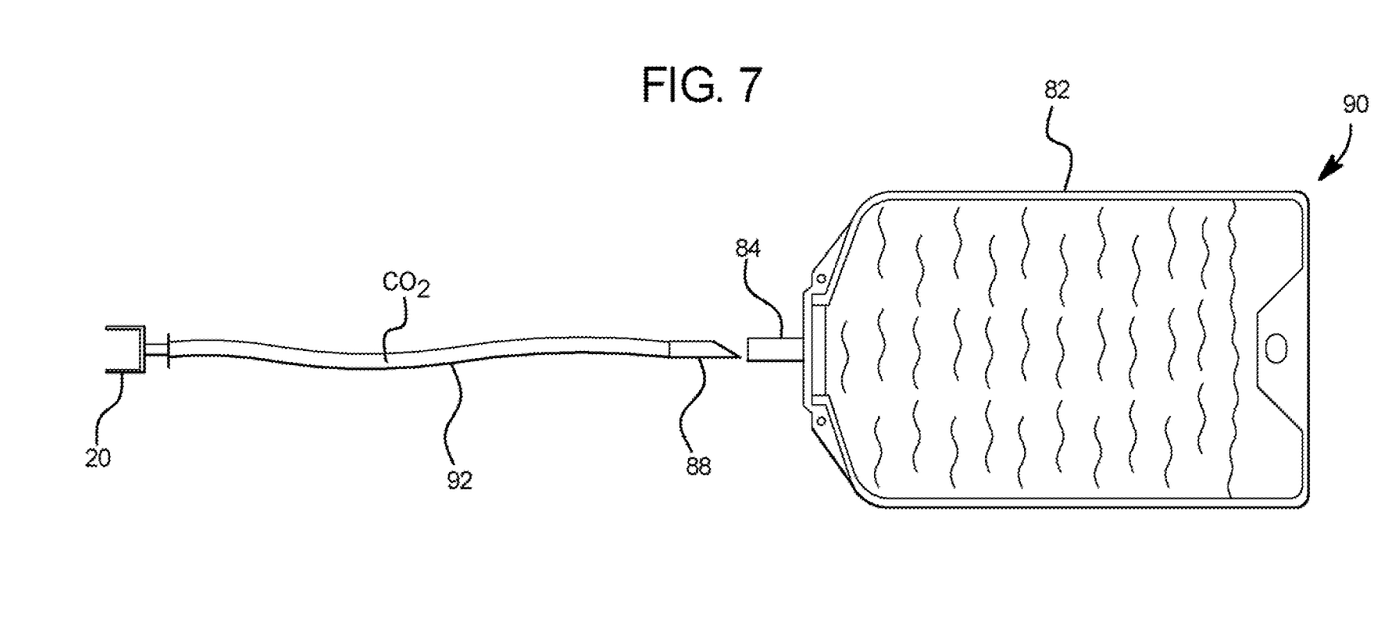
FIG. 7 is a side elevation view of one embodiment of a supply bag connected to a patient supply line that has been purged with a physiologically safe gas, such as carbon dioxide ("$CO_2$"), which is heavier than air and therefore readily purges air from the supply line.

Referring now to FIG. 7, apparatus 90 illustrates yet a further alternative embodiment for preventing air from a supply bag or supply tube from entering a patient's peritoneal cavity during a PD fill. Apparatus 90 includes solution bag 82 having a membrane-sealed delivery port 84 described above in connection with apparatus 80 of FIGS. 5 and 6A to 6D. Delivery port 84 is spiked via a spike 88 connected to a supply tube 92, which is capped via a membrane pierceable cap 20. Supply line 92 is filled with carbon dioxide ("$CO_2$"), which is a suitable gas from a number of standpoints. In a first instance, $CO_2$ is heavier than air such that filling supply tube 92 with $CO_2$ allows the $CO_2$ to "settle" within the tube and displace air or inert air from tube 92. Also, $CO_2$ is a gas that is common to the human body. The patient absorbs the $CO_2$ from tube 92 via the patient's peritoneum and exhales the $CO_2$ through the patient's lungs. $CO_2$ does not remain in the patient's peritoneum for days as does air.

Once the $CO_2$ is filled with line 92 and capped via cap 20 under a suitable sterilized environment, port 84 is spiked via spike 88 and seals around said spike, allowing the apparatus 90 to be delivered for use with a patient. It should be appreciated that spike end 88 is capped until the time for spiking membrane port 84, which can also be done under a suitable sterilizing environment. The entire apparatus 90 (connected or not connected) can then be sterilized via gamma radiation, ethylene oxide or steam sterilization.

Although not illustrated, spike 88 could be coupled alternatively to a check valve (or the check valve could be located at proximal end of line 92), allowing $CO_2$ filled line 92 and supply bag 82 to be shipped separately.

Figure 8:
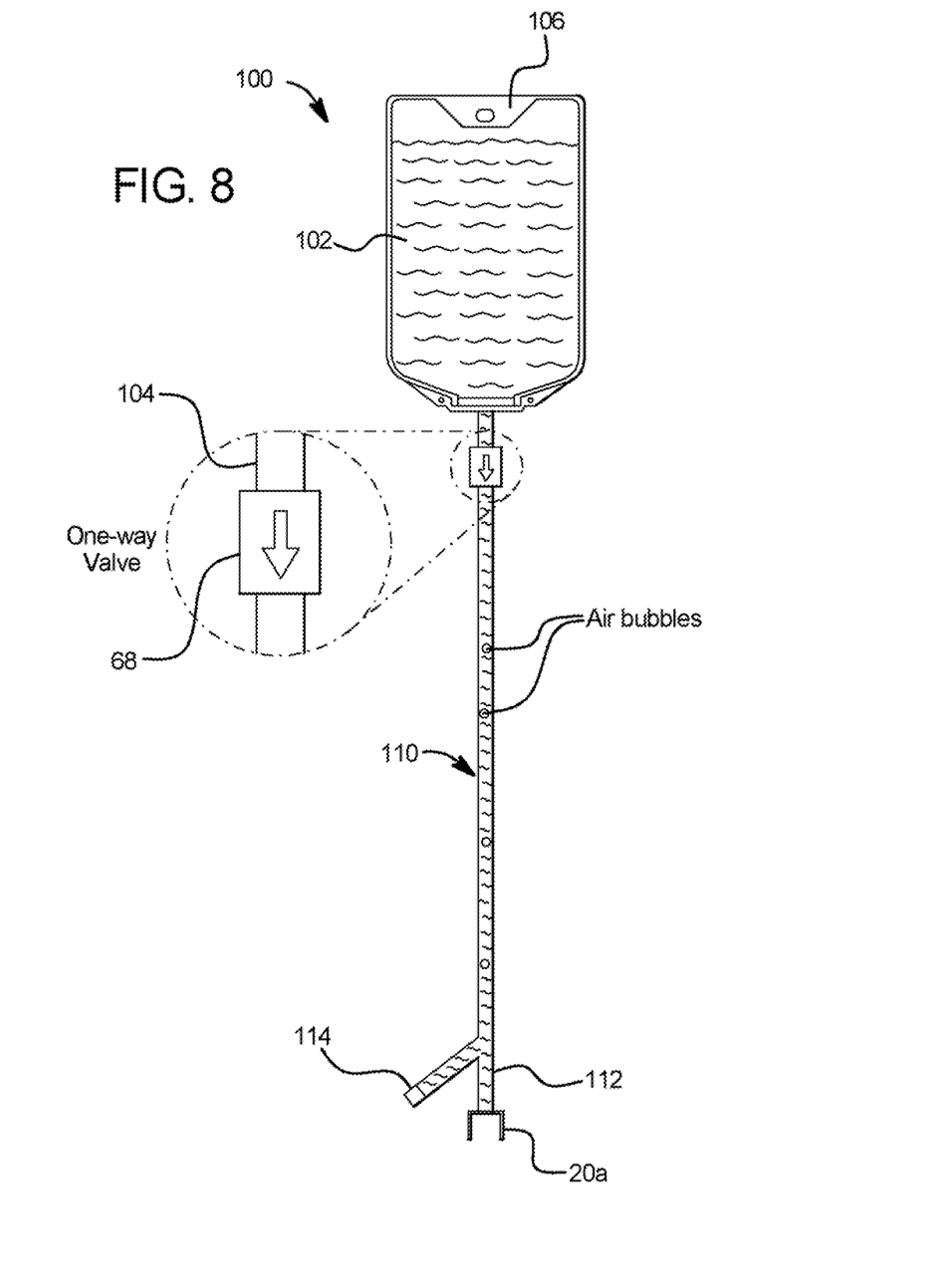
FIG. 8 is a side elevation view of one embodiment of a supply container connected to a patient's supply line, which has a Y-connection to a hydrophobic valve for purging air bubbles from the patient's supply line.

Referring now to FIG. 8, apparatus 100 illustrates yet a further alternative embodiment for preventing air from being delivered to the patient's peritoneal cavity during a PD fill. Apparatus 100 includes a supply bag or container 102 which includes a port 104 for sealed connection to a check or one way valve 68. Supply container 102 also includes a holder 106 for orienting bag 102 and associated supply line 110 during a purge process performed during the manufacture of apparatus 100.

Supply line 110 is connected sealingly to the outlet of check valve 68 and includes a y-connector 112 at its distal end. One branch of y-connector 12 terminates at a hydrophobic membrane or valve 114, which allows air but not dialysis solution to be passed through such membrane. One suitable hydrophobic membrane is provided by Millipore Corp., 290 Concord Road, Billerica, Mass. 01821, USA. The other end of the branch of y-connector 112 is capped via a pierceable membrane cap 20*a*, as has been described herein.

After the manufacturing and filling of apparatus 100, air bubbles will be trapped via one way valve 68 in supply line 100. Apparatus 100 is suspended vertically via holder 106, such that the weight of supply fluid within supply container 102 will flow through check valve 68 and force air out the bottom of y-connector 112 via hydrophobic valve 114. One-way valve 68 also prevents air remaining at the top of supply container 102 from permeating through the solution within the container and flowing into supply tube 110. That is, one-way valve 68 prevents liquid in the tube 110 from entering the bag, hence creating space for the air in the bag to enter the tube 110. When the purge of supply tube 10 is completed, hydrophobic valve is capped, e.g., under a suitable sterilized environment. Capping may also be done under non-sterile conditions, for example, when the hydrophobic filter pores are small enough to not allow pathogens from entering tube 110. The process of purging can therefore also be done at home by the patient. The entire apparatus 100 can then be sterilized, e.g., via gamma radiation, ethylene oxide or steam.

Figure 9:
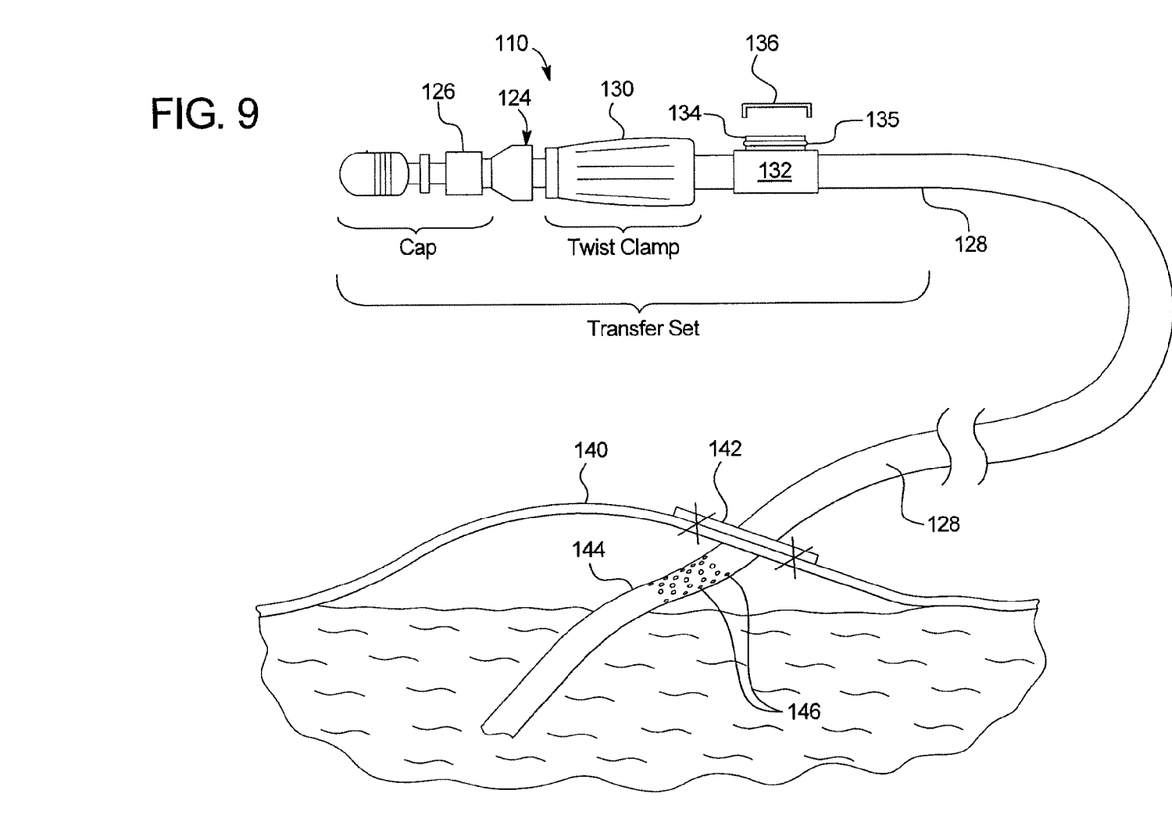
FIG. 9 is a side elevation view of one embodiment of a patient transfer set having a hydrophobic vent for enabling the patient to purge air from the patient's peritoneum during a peritoneal dialysis treatment.

Referring now to FIG. 9, apparatus 110 illustrates one apparatus and method for enabling the patient to remove air from the patient's peritoneal cavity when the patient feels discomfort. Apparatus 10 provides the fluid connection between the patient's transfer set and the patient as opposed to the fluid connection between the transfer set and the solution bag as has been described previously. Apparatus 110 can accordingly be operated with any of the other systems and apparatuses described herein.

Apparatus 110 includes a patient transfer set 124, which is capped in the illustrated embodiment via a cap 126. Cap 126 can be removed to expose a spike that spikes a sealed membrane cap 20*a* of a supply line, as has been described herein. Patient transfer set 124 also includes a twist clamp 130, which the patient turns to open or close fluid delivery to or from the patient's peritoneum. Apparatus 110 also illustrates a catheter 128, which extends from patient transfer set 124 the patient's peritoneal cavity.

Apparatus 110 further includes a t-type connector 132, which in the illustrated embodiment is spliced sealingly between patient tube 128 and twist clamp 130. Connector 132 could alternatively be formed as part of clamp 130 and be placed in sealed fluid communication with patient tube 128. Connector 132 includes a hydrophobic filter 134, which can be of the type described above for system 100 of FIG.

8. Hydrophobic filter 134 is fitted within a threaded connection, which receives a thread-on air tight cap 136. Cap and filter 134 can be sealed together via an o-ring 135 or other suitable seal, which for example fits either within the inside of cap 136 or fitted around the outside of hydrophobic filter 134. Cap 136 threads around the hydrophobic filter and seals the o-ring 135 to the body of the connector 132. Alternatively, cap 136 can snap-fit onto hydrophobic filter 134 and thereby comprise a seal.

Catheter 128 is fixed to patient 140 at access site 142 and catheter is implanted within patient 140. An implanted portion 144 of catheter 128 is formed with apertures or perforations 146 located along the catheter such that the apertures 146 are located within patient 140, directly adjacent access cite 142. Apertures 146 allow air that is trapped within patient 140 to enter catheter 144 and flow through patient tube 128, connector 132 and out filter or vent 134.

When the patient feels discomfort, the patient removes cap 136 from connector 132, exposing hydrophobic filter 134. Gas, including air, residing within the patient's peritoneal cavity is then able to migrate through the patient's PD catheter 128 and through hydrophobic filter to ambient. In this manner, a patient can remove air from the patient's peritoneal cavity without having to undergo the painstakingly long current procedure for removing such air. The patient can move around, lie down, sit up or perform some other exercise to help push the air within the patient's peritoneal cavity through the catheter, patient tube 128 and out filter 134. As seen in FIG. 9, perforations or holes are formed in the patient catheter, which when fixed to the patient locates the holes inside the patient near the access site. The perforations allow air to enter the catheter at one end (e.g., elevated end when the patient is lying down) of the patient's peritoneal cavity. When the patient no longer feels discomfort, the patient seals hydrophobic filter 134 with cap 136 and resumes treatment or other desired activity.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis ("PD") connection apparatus comprising:
a first connector including a connection end configured to be manually and removably connected to a PD fluid fill line;
a second connector in fluid communication with the first connector, the second connector including a filter configured to allow air but not fluid to pass through the filter;
a valve for selectively allowing fluid to flow to or from a patient's peritoneum, the valve separate from the filter and located between the filter and the connection end of the first connector when the first and second connectors are mated, such that air moving from the patient's peritoneum through the fluid fill line passes the filter before reaching the valve; and
an air-tight cap manually removable and resealable to the second connector so as to selectively expose the filter when the first connector is disconnected from the PD fluid fill line to (i) allow air trapped in the patient's peritoneum to be vented to atmosphere and (ii) prevent fluid from leaking from the patient's peritoneum.

2. The PD connection apparatus of claim 1, wherein the first and second connectors form part of a patient transfer set.

3. The PD connection apparatus of claim 2, wherein the valve is a twist clamp valve of the patient transfer set for selectively allowing fluid to flow to or from the patient's peritoneum.

4. The PD connection apparatus of claim 1, the first and second connectors in fluid communication with an implantable patient catheter, the catheter including at least one aperture located at a position of the catheter expected to be just inside a patient access site when the catheter is implanted, the at least one aperture allowing air trapped in the patient's peritoneum to enter the catheter to be vented to atmosphere via the filter.

5. The PD connection apparatus of claim 1, wherein the filter is a hydrophobic filter.

6. The PD connection apparatus of claim 1, wherein the air-tight cap is at least one of: (i) threaded onto the second connector over the filter; and (ii) sealed to the second connector via a compressible seal.

7. The PD connection apparatus of claim 6, wherein the compressible seal includes an o-ring carried by one of the cap and the second connector.

8. The PD connection apparatus of claim 1, wherein the second connector includes a branch extending from a fluid conduit portion of the connector, the branch housing the filter.

9. The PD connection apparatus of claim 1, which includes a cap fitted to the first connector when the first connector is disconnected from the fluid fill line.

10. The PD connection apparatus of claim 1, wherein the valve is provided with the first connector.

11. A peritoneal dialysis ("PD") connection apparatus comprising:
a connection end configured and arranged to be manually and removeably connected to a PD fluid fill line;
a filter placed in a branched relationship with respect to fluid flow through the PD connection apparatus, the filter allowing air but not fluid to pass through the filter; and
a valve separate from the filter and located between the connection end and the filter such that air moving from a patient's peritoneum through the fluid fill line passes the filter before reaching the valve, the valve for selectively allowing fluid to flow to or from the patient's peritoneum, the valve closeable to allow air to be purged via the filter even when the connection end is disconnected from the fluid fill line.

12. The PD connection apparatus of claim 11, which includes a removeable cap for exposing the filter.

13. The PD connection apparatus of claim 11, which includes a cap fitted to the connection end, the cap allowing air to be purged via the filter even when the connection end is disconnected from the fluid fill line and the valve is open.

14. The PD connection apparatus of claim 11, wherein the connection end, the filter and the valve are part of a patient transfer set.

15. The PD connection apparatus of claim 14, which includes an implanted catheter in fluid communication with the patient transfer set, the implanted catheter including at least one aperture located at a position of the catheter expected to be just inside a patient access site when the catheter is implanted, the at least one aperture allowing air trapped in the patient's peritoneum to enter the catheter to be vented to atmosphere via the filter.

16. The PD connection apparatus of claim 11, which includes a first connector connectable to a second connector, the first connector including the connection end and the valve, the second connector including the filter.

\* \* \* \* \*